United States Patent [19]

Carter

[11] Patent Number: 5,339,807
[45] Date of Patent: Aug. 23, 1994

[54] EXHALATION VALVE STABILIZING APPARATUS

[75] Inventor: Danis Carter, Escondido, Calif.

[73] Assignee: Puritan-Bennett Corporation, Carlsbad, Calif.

[21] Appl. No.: 949,073

[22] Filed: Sep. 22, 1992

[51] Int. Cl.$^5$ ............................................. A62B 9/02
[52] U.S. Cl. ........................... 128/205.24; 128/204.21; 128/204.23
[58] Field of Search ................ 128/204.18, 204.21, 128/204.23, 205.24

[56] References Cited

U.S. PATENT DOCUMENTS

| | | | |
|---|---|---|---|
| 4,020,834 | 5/1977 | Bird | 128/204.25 |
| 4,527,557 | 7/1985 | DeVries et al. | 128/204.23 |
| 4,838,257 | 6/1989 | Hatch | 128/204.21 |
| 5,072,729 | 12/1991 | DeVries | 128/204.23 |
| 5,127,400 | 7/1992 | DeVries et al. | 128/205.24 |

Primary Examiner—Edgar S. Burr
Assistant Examiner—Aaron J. Lewis
Attorney, Agent, or Firm—Fulwider Patton Lee & Utecht

[57] ABSTRACT

The movements of an exhalation valve are damped at a variable rate to control pressure oscillations within a ventilation system. The exhalation valve is damped as a function of its velocity at a rate that is a function of a variable linked to the pneumatic state of the system, to provide a feedback signal to the valve driver.

19 Claims, 3 Drawing Sheets

EXHALATION VALVE STABILIZING APPARATUS

BACKGROUND OF THE INVENTION

1. Field of the Invention

The present invention relates generally to breathing ventilators, and more particularly concerns the control of the exhalation valve during the breathing cycle.

2. Description of the Related Art

Lung ventilation systems provide artificial respiration to patients whose breathing ability is impaired. Typically, such systems are capable of operating in any of several modes, selectable as a function of the degree of breathing assistance prescribed for a particular patient. At one extreme, the ventilator is given complete control including when each breath is delivered and the volume of gases delivered during each breathing cycle. At the other extreme, the ventilator permits "spontaneous" breathing wherein the inspiration and expiration phases are commenced in response to efforts by the patient. Varying degrees of control within these two extremes can be taken advantage of.

System pressure, both during the inspiration phase as well as the expiration phase is controlled by the exhalation valve. During inspiration, the exhalation valve in effect serves as a pressure relief valve to limit to a preselected value the maximum pressure the patient is exposed to. Upon exhaling, the breath is expelled through the exhalation valve, which during the expiration phase attempts to maintain pressure at a lower preselected second value.

An important parameter which is controlled by the ventilator during spontaneous as well as fully automated modes of ventilation is the residual pressure against which the patient exhales. It has been found that by maintaining a slight positive pressure, the collapse of alveoli, the bronchial passages and possibly the entire lung in severely compromised patients, can be prevented. As a patient regains strength, the positive end expiratory pressure (PEEP) is gradually reduced until finally each breath is expelled against only ambient pressure and the patient is fully weaned from the ventilator.

Problems arise upon transitioning from the inspiration phase to the expiration phase as the "command" pressure maintained by the exhalation valve is abruptly lowered from the desired inspiration pressure to the desired PEEP, and the patient begins to exhale. In a conventional ventilator system, the actual system pressure initially drops off precipitously to oscillate about the desired PEEP until ultimately equilibrating at a further reduced pressure. Such oscillation or "ringing" occurs at the natural frequency intrinsic to the particular system. The compressibility and volume of the respiratory gas, the flexibility and resiliency of the ventilator system's componentry and associated plumbing in contact with the gas as well as the patient's own physical constitution are all factors that influence the frequency and amplitude of this oscillation. Depending on the characteristics of a particular system, the amplitudes of oscillation can be substantial and the oscillations can continue for a significant portion of the expiration phase.

It is most desirable to minimize the described pressure oscillations and preferable to eliminate them altogether. Oscillation troughs below the desired PEEP level, albeit of short duration may have an adverse physiological effect due to the under pressurization of the alveoli structure. Additionally, such periods of reduced pressure may be misinterpreted by the ventilator system as an attempt by the patient to initiate a breath and may thereby auto-trigger a premature inspiration phase. Pressure peaks above the desired PEEP level, albeit of similarly short duration, require the patient to labor against excessive pneumatic pressures in an effort exhale. Additionally, the pressure excursions above the desired PEEP level cause the exhalation valve to open in an effort to maintain the desired PEEP which in doing so allows an excessive volume of gas to escape resulting in a ultimately lower than desired PEEP upon equilibration. The reduced PEEP is again undesirable for the physiological reasons set forth above as well as possibly causing the initiation of a premature auto-triggering of the inspiration phase.

Instability during inspiration is similarly undesirable. Fluctuations above command pressure may be misinterpreted as an attempt by the patient to exhale and could thereby auto-trigger a premature exhalation phase. Excursions below command pressures are indicative of a less than desired rate of air delivery into the lungs.

Previous attempts to control these oscillations within the ventilation system have focused on controlling the exhalation valve and have included efforts to reduce the lag time inherent in the operation of the valve itself as well as the damping of the valve's movements. Systems have been proposed wherein valve movement is damped at a constant rate such that the damping force is a direct function of a single variable such as system pressure, valve velocity or gas flow rate.

Although prior art efforts have reduced somewhat the described undesired pressure oscillations in the ventilator system, further reduction is desirable. Ideally, ventilator system pressure should closely follow, without significant deviation, the command pressure curve at all times, especially the step profile linking the relatively elevated plateau during inspiration to the lower PEEP plateau.

SUMMARY OF THE INVENTION

The present invention overcomes the shortcomings of prior art ventilation systems to provide for an exhalation phase without the above-described undesirable pressure oscillations. This is achieved via the exhalation valve and more specifically by variably damping the motions of the valve. In accordance with the invention, the motions of the exhalation valve are damped at a variable rate, such that damping forces exerted on the valve are a function of valve velocity at a rate that is in turn a function of an additional variable. Such additional variable is selected from variables intimately related to the pneumatic state of the system, such as system pressure or respiratory gas flow rate.

The valve is subject to a number of forces upon activation. Both system pressure and gravity act to open the valve while a drive mechanism exerts an opposing force to close the valve. A controller causes a current to flow in the valve coil of the drive mechanism. This current causes a predictable electromagnetic force to be generated which opposes the motor magnets, thereby forcing the bobbin to move. This force, times the bobbin area results in a predictable pressure.

The present invention focuses on the resultant motion of the valve subject to these various forces and causes the force exerted by the drive mechanism to be either increased or decreased to a degree commensurate with the valve's velocity, as well as with the value of the selected pneumatic variable. More particularly, a signal representative of the valve's velocity, multiplied by a signal representative of the instantaneous value of the selected pneumatic variable is summed with the command signal generated by the controller to produce an actuating signal to which the valve driving mechanism is responsive. The modification of the command signal in this manner has the effect of damping the motion of the valve.

The damping of the motions of the exhalation valve in accordance with the present invention in turn has the effect of significantly minimizing the oscillations of pressure such systems were heretofore subject to especially upon initiation of the exhalation phase. As a result, the actual system pressure very closely follows the command pressure curve. The patient is therefore able to exhale against a very constant and undiminished PEEP and without inadvertent auto-triggerings of an inspiration phase. Similarly, inspiration is very constant without inadvertent auto-triggerings of an exhalation phase.

These and other features and advantages of the present invention will become apparent from the following detailed description of a preferred embodiment which, taken in conjunction with the accompanying drawings, illustrates by way of example the principles of the invention.

DETAILED DESCRIPTION OF THE DRAWINGS

DETAILED DESCRIPTION OF THE PREFERRED EMBODIMENT

The present invention is concerned with the stabilization of the respiratory pressure of a patient subject to artificial lung ventilation. Such ventilation systems provide for various degrees of breathing assistance ranging from fully automated modes wherein a preselected volume of gas is forced into a patient's lungs during a preselected period of time at preselected intervals to modes wherein both the inhalation as well as expiration (exhalation) phases are initiated by the patient. The exhalation valve ultimately controls pressure during all phases of respiration. During inhalation, the valve maintains an elevated pressure to allow the patient's lungs to be inflated. During exhalation, the valve maintains a substantially reduced pressure (0–45 cm H2O), as has been found to be advantageous for various physiological reasons. Residual pressure maintained during exhalation is referred to as positive end expiratory pressure (PEEP).

Figure 1:
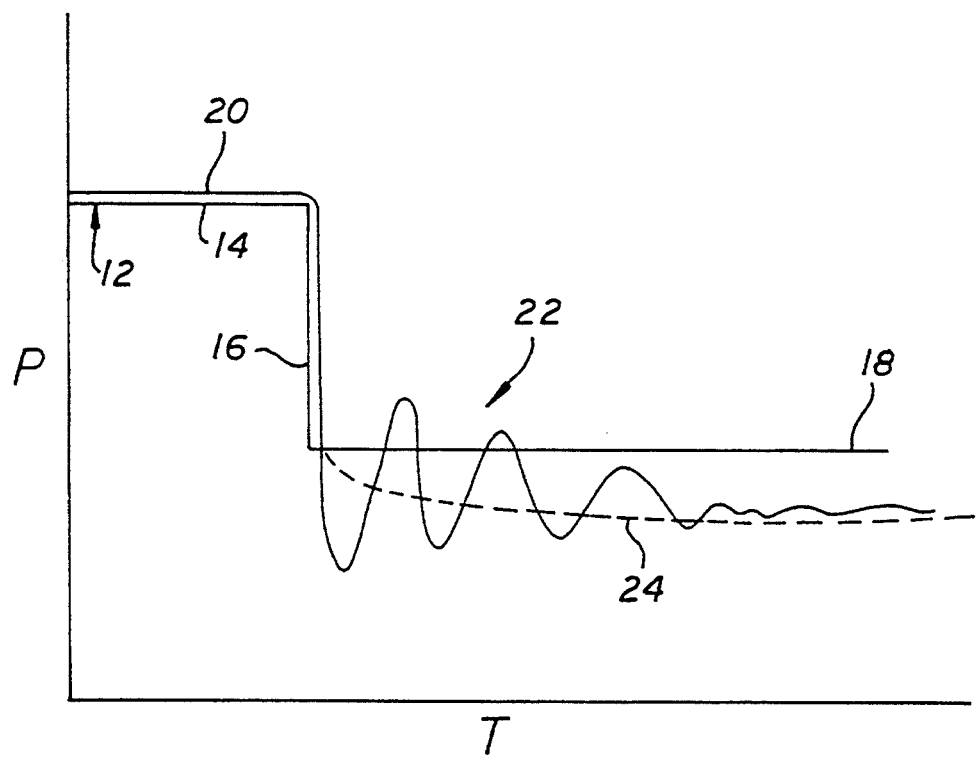
FIG. 1 is a graph illustrating the pressure response of a ventilation system during exhalation without benefit of the present invention.

Ventilation systems not having benefit of the present invention suffer from a "ringing" of system pressure both upon initiation of an exhalation phase as well as upon initiation of an inspiration phase. FIG. 1 is a representative illustration of the phenomenon during exhalation wherein system pressure (P) is plotted as a function of time (t). The stepped curve 12 is the command pressure, i.e. the desired pressure which the ventilation system attempts to maintain. The upper plateau 14 is the pressure maintained during inspiration while respiratory gases are being forced into the lungs. The lower plateau 18 represents the desired PEEP to be maintained during exhalation. A substantially vertical transition 16 separates the two plateaus. Curve 20 represents the actual pneumatic pressure which near the tail end of inspiration fairly faithfully follows the command pressure plateau 14. Upon the initiation of expiration, the exhalation valve opening is suddenly increased, which causes the pressure to drop off percipituously. As the command PEEP 18 is approached, the exhalation valve is closed. However, due to a number of factors related to the function of the valve and the resiliency of the entire system, a subsequent "ringing" 22 of the system is observed. Any delay in valve closure as actual pressure drops below command PEEP and any opening of the exhalation valve as the system rebounds above command PEEP causes an excessive loss of respiratory gas which manifests itself as an actual PEEP below command PEEP. The dotted line 24 represents system pressure at equilibrium and shows a gradual decline of actual PEEP below command PEEP.

Figure 2:
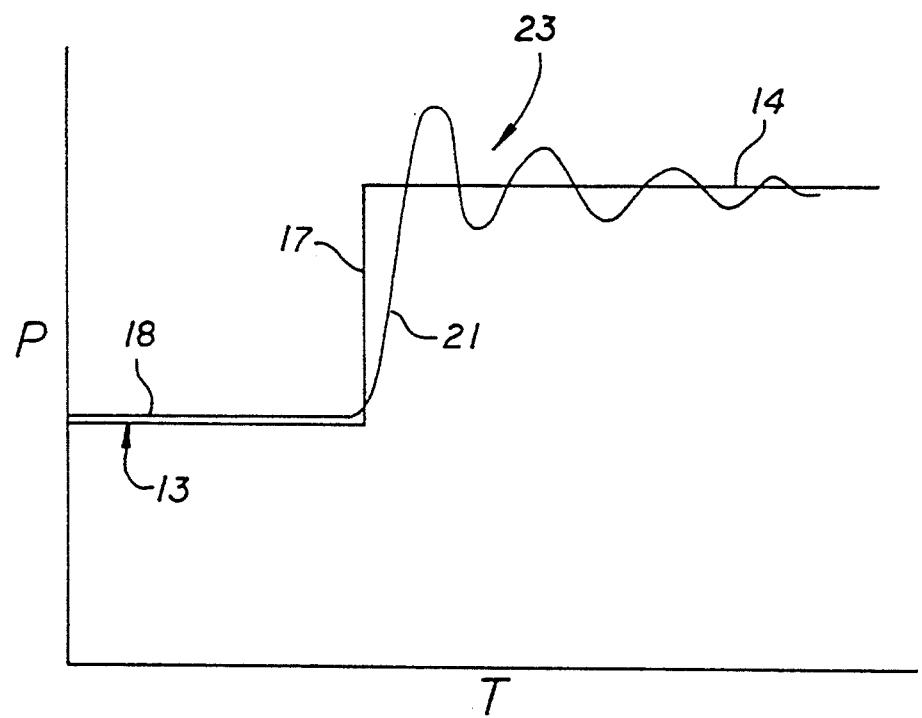
FIG. 2 is a graph illustrating the pressure response of a ventilation system during inspiration without benefit of the present invention.

FIG. 2 is a representative illustration of the ringing phenomenon during inspiration. A substantially vertical transition 17 links the two plateaus of the command curve 13. As the command inspiration pressure 14 is approached, the exhalation valve is opened. For reasons very similar to those responsible for the ringing during exhalation, the actual pneumatic pressure 21 is the subject to a ringing 23.

Figure 3:
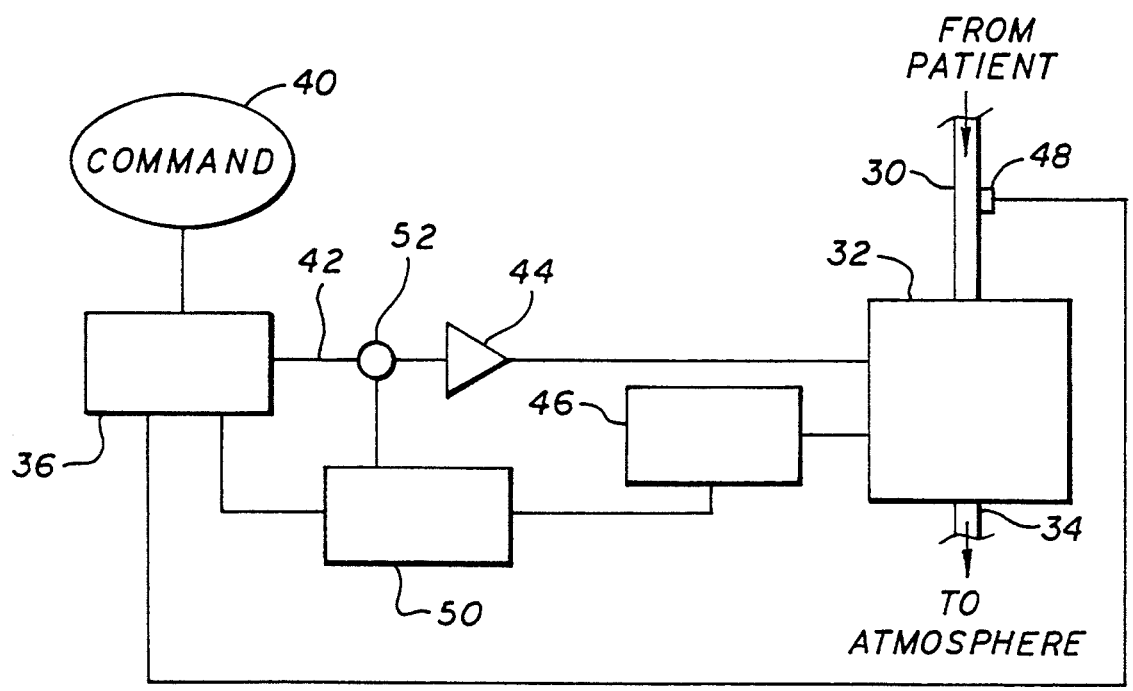
FIG. 3 is a schematic representation of the ventilation system of the present invention.

FIG. 3 schematically illustrates the ventilation system of the present invention. Airway 30 extends from the patient and is at all times subject to the prevailing respiratory pressure. Exhalation valve 32 regulates the venting of respiratory gas therethrough to atmosphere and is consequently relied upon to regulate respiratory pressure within the entire system including the patient's lungs and airways.

Controller 36 generates signals that control the force produced by the valve as well as the dampening rate. Velocity transducer 46 generates a signal representative of any movement the valve undergoes to reflect both the direction and magnitude of such movement. Transducer 48 generates a signal representative of a pneumatic variable. In the preferred embodiment, element 48 comprises a flow transducer although other parameters pertaining to the pneumatic state of the respiratory system can be substituted. The use of system pressure has also been found useful for the purposes of the invention, in which case an additional transducer is not required as system pressure can be inferred from the current flowing through the valve actuation coil.

The multiplier 50, multiplies the signal generated by velocity transducer 46 by the dampening command rate generated by controller 36 to provide a damping signal which is then summed at summing junction 52 with the command signal issued by controller 36. Signal gain amplifier 44 subsequently amplifies the modified command signal or actuation signal to provide an actuation current for driving the valve mechanism.

Figure 4:
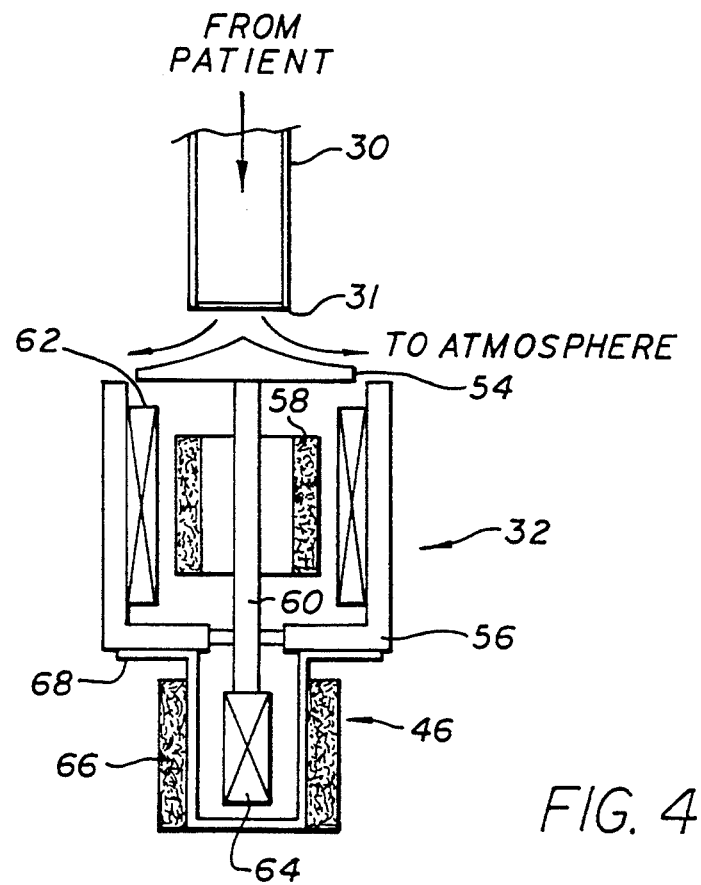
FIG. 4 is a schematic illustration of the exhalation valve according to the present invention.

FIG. 4 illustrates the valve and velocity transducer assembly in semi-schematic form. Poppet valve 54 is variably positionable so as to regulate the flow of respiratory gas past valve seat 31 from airway 30 that extends from the patient. The poppet is positioned by a solenoid that includes a motor coil 58 affixed about the valve stem 60 and motor magnets 62 positioned within a housing 56. Energization of coil 58 causes poppet valve 54 to be driven upwardly. De-energization allows gravity and pneumatic pressure in line 30 to drop the valve away from the valve seat.

A velocity transducer magnet 64 is attached to distal end of valve stem 60. The magnet is surrounded by velocity transducer coil 66 which is held in position by transducer housing 68 affixed to valve housing 56. Any movement of magnet 64 relative transducer coil 66 induces a voltage. The resulting voltage is both indicative of the direction and magnitude of the movement.

In operation, the expiration phase is commenced with the lowering of the command pressure. In fully automated modes of operation, the initiation of this event is fully automated, subject to a preselected time sequence. In "spontaneous" breathing modes this event is triggered by a sudden increase of respiratory pressure, representative of a patient's attempt to exhale. In comparing the new lower command pressure level to the much higher actual respiratory pressure of the filled lungs, the controller immediately reduces the current energizing the valve solenoid. The force of gravity and the pneumatic pressure acting against the valve 54 causes the valve to drop away thereby increasing the gap between valve 54 and valve seat 31 to allow the respiratory gases to be expelled. As the actual pressure drops and begins to approach command pressure, the valve force balance moves the valve upwardly in order to reduce the valve opening. Any movement of the valve induces a voltage in transducer coil 66. Such voltage is multiplied by the dampening rate signal produced by the controller which is a function of the selected pneumatic variable. The resulting voltage is subsequently summed with the voltage representing the target force. Upward movement of the valve induces a corresponding voltage in the velocity transducer which when inverted and multiplied by the dampening signal, provides a net negative damping signal. The negative damping signal summed with the signal generated by the controller serves to reduce the signal amplified by amplifier 44 which reduces the current flowing to the valve solenoid and thereby retards the valve's movement. In the event the controller causes the valve to increase its opening slightly in order to reduce pressure further, the downward movement of the valve induces a negative voltage in transducer 46, which when, inverted and multiplied by a positive pressure signal from transducer 48, produces a positive signal for summing with the signal issued by the controller to increase the actuation current and thereby retard the valve's downward movement.

Figure 5:
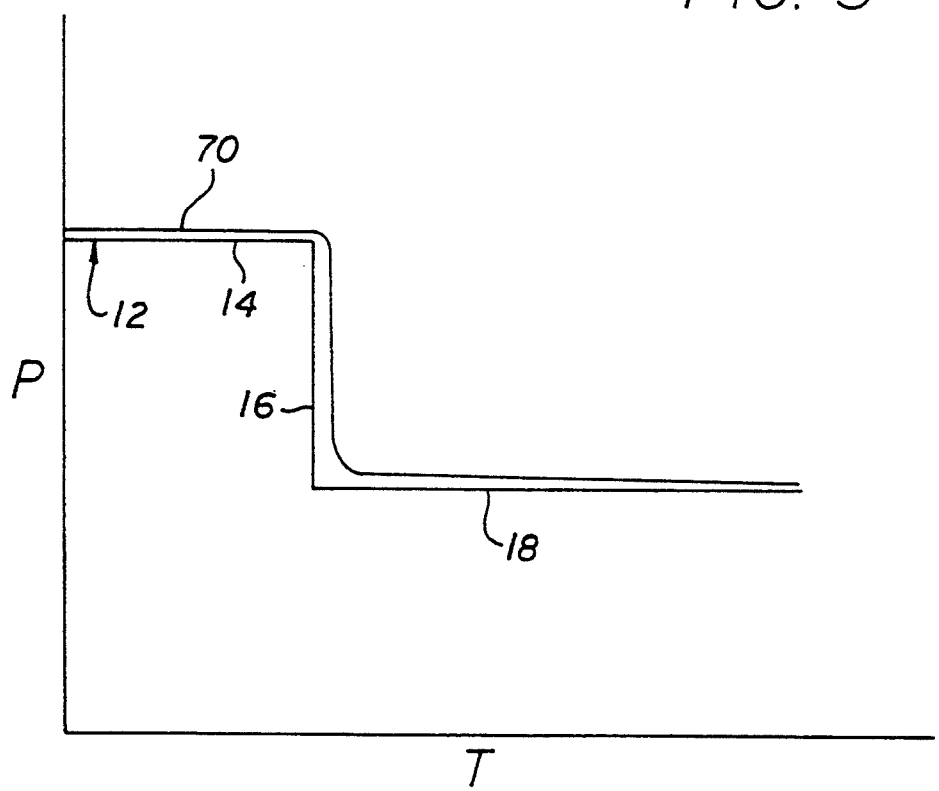
FIG. 5 is a graph illustrating the pressure response during exhalation of the ventilation system according to the present invention.
Figure 6:
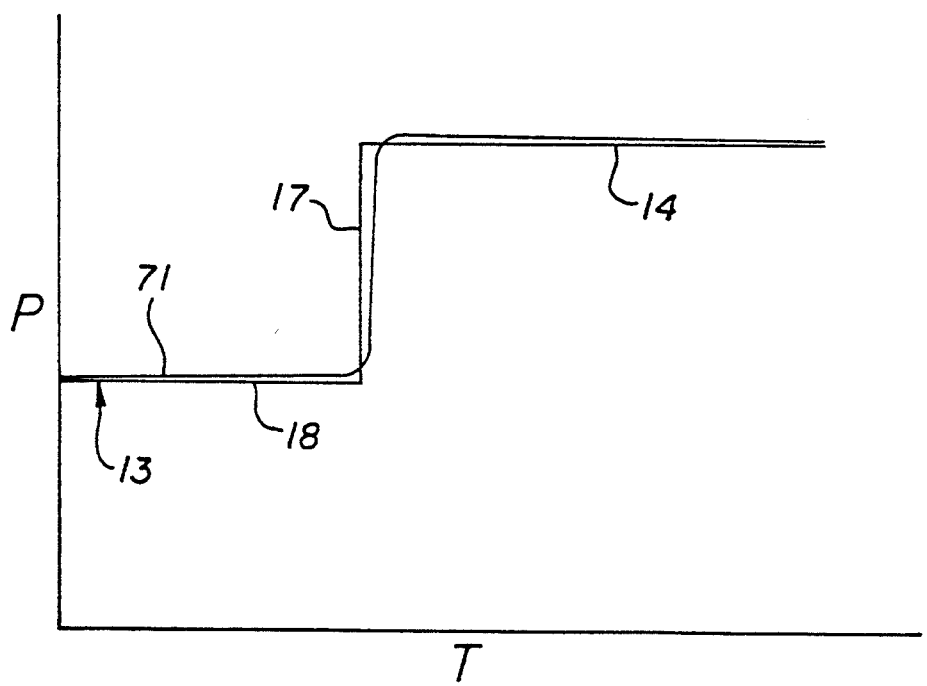
FIG. 6 is a graph illustrating the pressure response during inspiration of the ventilation system according to the present invention.

Adjusting the damping rate as a function of pressure has the effect of providing an altered damping rate for higher pneumatic pressures. Such damping characteristics in conjunction with a relatively high gain amplification affords superior control of system pressure and as is illustrated by system pressure curves 70 and 71 in FIGS. 5 and 6, substantially prevents the pressure fluctuations heretofore associated with ventilation systems lacking a variably damped exhalation valve.

While a particular form of the invention has been illustrated and described, it will also be apparent to those skilled in the art that various modifications can be made without departing from the spirit and scope of the invention. Accordingly, it is not intended that the invention be limited except by the appended claims.

What is claimed is:

1. A lung ventilation system employing a variably positionable exhalation valve wherein the position of said valve is determinative of the rate of venting of respiratory gases from said system, comprising:
   means for repositioning said valve to compensate for deviations of system pressure from a preselected value; and
   means for damping the rate of such repositioning at a variable rate,
   wherein the repositioning of said valve is damped as a function of the product of a signal representative of the rate of repositioning and of a signal related to the instantaneous value of a pneumatic variable.

2. A lung ventilation system employing a variably positionable exhalation valve wherein the position of said valve is determinative of the rate of venting of respiratory gases from said system, comprising:
   means for repositioning said valve to compensate for deviations of system pressure from a preselected value; and
   means for damping the rate of such repositioning at a variable rate,
   wherein the repositioning of said valve is damped as a function of the product of a signal representative of the rate of repositioning and of a signal related to the instantaneous value of a pneumatic variable,
   wherein said pneumatic variable comprises system pressure.

3. A lung ventilation system employing a variably positionable exhalation valve wherein the position of said valve is determinative of the rate of venting of respiratory gases from said system, comprising:
   means for repositioning said valve to compensate for deviations of system pressure from a preselected value; and
   means for damping the rate of such repositioning at a variable rate,
   wherein the repositioning of said valve is damped as a function of the product of a signal representative of the rate of repositioning and of a signal related to the instantaneous value of a pneumatic variable.
   wherein said pneumatic variable comprises gas flow.

4. A lung ventilation system employing a variably openable exhalation valve for controlling the venting of respiratory gas from said system, comprising:
   means for generating a command signal for effecting a variation in said valve opening in order to adjust system pressure to a preselected level;
   valve opening varying means responsive to an actuation signal;
   velocity transducing means for measuring the variation rate of said exhalation valve opening and generating a signal representative thereof;
   pneumatic variable transducing means for measuring the value of a preselected pneumatic variable and generating a signal representative thereof;
   means for modulating said velocity signal with a signal proportional to said pneumatic variable, to yield a damping signal; and means for combining said command signal with said damping signal to yield said actuation signal.

5. The system of claim 4 wherein said modulating means is a multiplier device operative to multiply the velocity signal by said signal proportional to said pneumatic variable.

6. The system of claim 5 wherein said combining means comprises a summing device wherein said damping signal is added to said command signal.

7. The system of claim 6 wherein said pneumatic variable comprises system pressure.

8. A lung ventilation system, comprising:
an exhalation valve for venting respiratory gas from said system including a poppet and seat arrangement wherein said poppet is biased away from said seat and a valve closing means is provided, operative to drive said poppet toward said valve seat in response to a variable degree of energization of said valve closing means;
means for generating a velocity signal representative of the velocity of said poppet;
means for generating a pneumatic variable signal representative of the instantaneous value of such variable;
means for modulating said velocity signal with a value proportional to said pneumatic signal to yield a damping signal;
means for modifying the degree of energization with said damping signal so as to damp the movement of the poppet whereby pressure fluctuations relative a preselected pressure level within said system are damped.

9. The system of claim 8 wherein said poppet is biased away from said seat by the force of gravity in addition to system pressure.

10. The system of claim 9 wherein the valve closing means comprises a solenoid.

11. The system of claim 10 wherein said velocity signal generating means comprises:
a magnet affixed to the poppet; and
a coil disposed in a position about said magnet such that movement of said poppet generates an electrical signal within said coil in proportion to the direction and magnitude of such movement.

12. The system of claim 10 wherein said modulating means comprises a multiplier device operative to multiply said the velocity signal by the pneumatic variable signal to yield said damping signal;
means for varying the degree of energization in order to compensate for deviations of system pressure from a preselected pressure level; and
means for adding the damping signal.

13. The system of claim 12 wherein said pneumatic variable comprises system pressure.

14. The system of claim 13 wherein said pneumatic variable comprises system pressure.

15. The system of claim 13 wherein said pneumatic variable comprises gas flow.

16. A lung ventilation system employing a variably positionable exhalation valve wherein the position of said valve is determinative of the rate of venting of respiratory gases from said system, comprising:
means for repositioning said valve to compensate for deviations of system pressure from a preselected value; and
means for damping the rate of repositioning of said valve at a variable rate,
wherein said rate of damping is a function of the rate of repositioning and a damping value, said damping value being a function of a pneumatic variable.

17. The system of claim 16, wherein said rate of damping is a function of the product of a signal representative of the rate of repositioning and of a signal related to the instantaneous value of said pneumatic variable.

18. The system of claim 17, wherein said pneumatic variable comprises system pressure.

19. The system of claim 17, wherein said pneumatic variable comprises gas flow.

* * * * *

UNITED STATES PATENT AND TRADEMARK OFFICE
CERTIFICATE OF CORRECTION

PATENT NO. : 5,339,807
DATED : August 23, 1994
INVENTOR(S) : Danis Carter It is certified that error appears in the above-identified patent and that said Letters Patent is hereby corrected as shown below:

In Column 8, line 5, delete "claim 10", insert --claim 8--.

Signed and Sealed this

Fourteenth Day of February, 1995

Attest:

BRUCE LEHMAN

*Attesting Officer*  *Commissioner of Patents and Trademarks*